(12) United States Patent
Rouseff et al.

(10) Patent No.: US 8,372,443 B2
(45) Date of Patent: Feb. 12, 2013

(54) METHODS AND COMPOSITIONS FOR THE TREATMENT AND PREVENTION OF CITRUS GREENING DISEASE

(75) Inventors: Russell L. Rouseff, Winter Haven, FL (US); Lukasz L. Stelinski, Lake Alfred, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 450 days.

(21) Appl. No.: 12/547,095

(22) Filed: Aug. 25, 2009

(65) Prior Publication Data
US 2010/0074972 A1 Mar. 25, 2010

Related U.S. Application Data

(60) Provisional application No. 61/091,500, filed on Aug. 25, 2008.

(51) Int. Cl.
*A01N 59/02* (2006.01)
*A61K 33/04* (2006.01)

(52) U.S. Cl. .................................................. 424/712
(58) Field of Classification Search .................... 424/712
See application file for complete search history.

(56) References Cited

U.S. PATENT DOCUMENTS

| 3,300,535 A | 1/1967 | Hession | |
| 4,447,447 A * | 5/1984 | Hreschak et al. | 514/473 |

OTHER PUBLICATIONS

Gottwald, T. et al., Citrus Huanlongbing: The Pathogen and Its Impact, Plant Health Progress, Sep. 6, 2007.*
Idstein et al., Volatile Constituents from Guava (*Psidium guajava*, L.) Fruit, J Agric Food Chem 33: 138-143 (1985).*
Salas, J., Efficacy of a garlic based repellent on the reduction of whitefly (*Benusua tabacu*) populations, Agronomia Tropical (Maracay) 51: 163-174 (2001).*
Auger, J. et al., Leek odour analysis by gas chromatography and identification of most active substance for leek moth *Acrolipeopsis assectella*, J Chemical Ecol 15: 1847-1854 (1989).*
Beattie et al., Aspects and Insights of Australia-Asia Collaborative Research on Huanglongbing, Proc Intl Workshop Prevention of Citrus Greening Disease in Severely Infected Areas, Intl. Res. Div, Agric. Forestry Fisheries Res. Council Secretariat, Ministry of Agric. Forestry and Fisheries, Tokyo, Japan, pp. 47-64 (2006).*
Gottwald et al. Citrus Huanglongbing: The Pathogen and its impart. Plant Health Progress doi:10.1094/PHP-2007-0906-01-RV pp. 1-36. Published Sep. 6, 2007, p. 30 para 1.
Idstein et al. Volatile Constitutents from Guava (*Psidium guajava*, L.) Fruit. J. Agric. Food Chem., 1985, vol. 33, No. 1, pp. 138-143, p. 139 Table 1.

* cited by examiner

*Primary Examiner* — Robert T Crow
*Assistant Examiner* — Thor Nielsen
(74) *Attorney, Agent, or Firm* — Timothy H. Van Dyke; Beusse, Wolter, Sanks, Mora & Maire, P.A.

(57) ABSTRACT

The present invention is directed to methods and compositions for the prevention of citrus greening disease. In one embodiment, there is provided a method for repelling or killing insect vectors of citrus greening disease comprising exposing the vectors to an effective amount of at least one volatile compound set forth in Tables 1 and 2 herein. In one embodiment, the volatile compound is dimethyl disulfide.

8 Claims, 6 Drawing Sheets

METHODS AND COMPOSITIONS FOR THE TREATMENT AND PREVENTION OF CITRUS GREENING DISEASE

CROSS-REFERENCE TO RELATED APPLICATIONS

This application claims the benefit of U.S. Provisional Application No. 61/091,500, filed Aug. 25, 2008, the entirety of which is hereby incorporated by reference in its entirety.

FIELD OF THE INVENTION

The present invention relates to insecticide compositions, and more particularly to insecticide compositions comprising newly identified volatile compounds, and to methods for repelling or killing vectors of citrus greening disease using such volatile compositions.

BACKGROUND OF THE INVENTION

Huanglongbing, HLB, or citrus greening disease was first reported in southern China in 1919 (Reinkinget, al., 1919), but it has been suggested to have originated in Africa. The disease is now found in approximately 40 different Asian, African, North and South American countries and has recently become a serious threat in Florida, California, Louisiana, Texas and Brazil, all of which are major citrus producing locations. Citrus greening disease is caused by the phloem-limited fastidious prokaryotic α-proteobacterium *Candidatus Liberibacter* spp., *Ca. africanus*, and *Ca. L. americanus*. Two psyllids, *Diaphorina citri* Kuwayama and *Trioza erytreaei*, are known to vector the disease (Manjunath, et al., 2002). Citrus trees that become infected with the devastating citrus greening disease go into decline, producing mishappened, off-flavor fruit, and then die within a few years. The $1.4 billion annual Florida citrus industry (Ewing, et al., 2006-2007) is severely threatened by this vector-disease pathosystem. Further, the disease threatens to wipe out the $1.3 million annual citrus industry in California. Presently, there is no cure for this disease and trees are routinely destroyed once severely infected. Moreover, there are no known relevant cultivars that are resistant to citrus greening disease. Since 2005, it is estimated that about 650,000 trees have been destroyed in Brazil and a similar number in Florida to slow the disease.

1. BRIEF DESCRIPTION OF THE FIGURES

Figure 4:
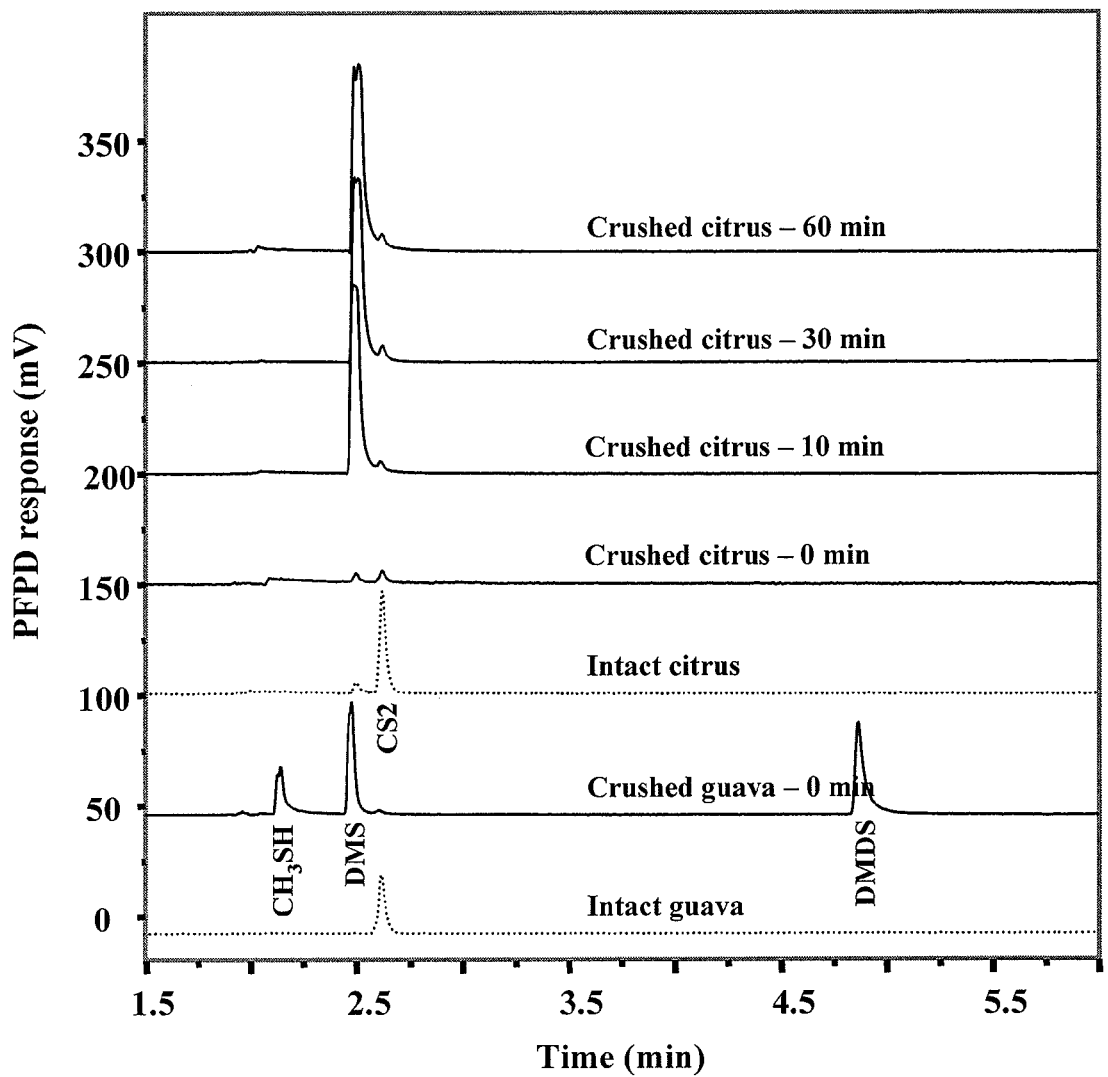

FIG. 4 is a comparison showing chromatograms of sulfur volatiles from guava and citrus flush. The chromatograms depict sulfur volatiles from intact and crushed guava compared with those of intact and crushed citrus. To compile the chromatographic results, static head-space volatiles were collected from either intact guava or citrus flush after equilibrating the samples at ambient laboratory conditions for ~30 min, or at various durations after mechanical damage (0, 10, 30 or 60 min). GC-PFPD responses (mV) are shown on the Y-axis and retention time (min) on the x-axis.

Figure 5:
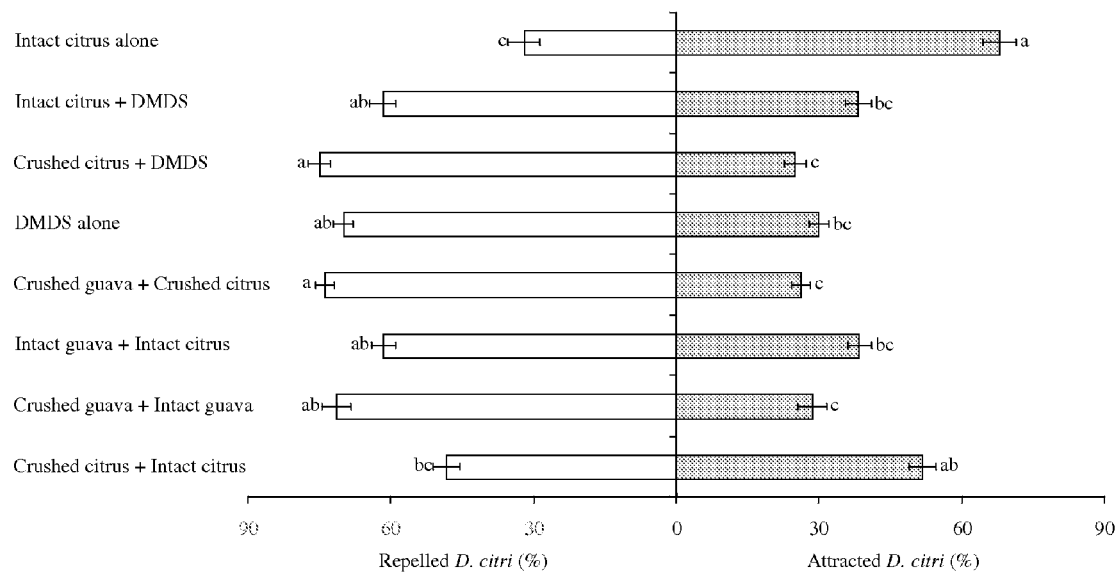

FIG. 5 is a comparison showing responses of *D. citri* to volatiles emanating from intact citrus, crushed citrus and DMDS, DMDS only, crushed guava and crushed citrus, intact guava and intact citrus, crushed guava and intact guava, and crushed citrus and intact citrus in the 4-choice olfactometer. Grey bars represent the percentage of *D. citri* attracted while white bars represent percentage repelled. White or grey bars followed by the same letters are not significantly different (Tukey's HSD test, P<0.05).

FIGS. 6a-6b are comparisons showing responses of *D. citri* to volatiles in a Y-tube olfactometer when presented with volatiles emanating from intact citrus alone (Citrus) or intact citrus and DMDS (Citrus+DMDS) in both arms of the olfactometer. Grey bars represent the percentage of repelled *D. citri* while white bars represent percentage of attracted *D. citri* (a); Responses of *D. citri* when presented with laboratory air in one arm of the olfactometer versus volatiles emanating from intact citrus (citrus) or DMDS in mineral oil (DMDS) in the other (b). Grey bars represent the percentage of repelled *D. citri* while white bars represent the percentage of attracted *D. citri*.

DETAILED DESCRIPTION OF THE INVENTION

The inventors of the present invention have unexpectedly found that the volatile compounds, which are released by the common guava (*Psidium guajava* L.) have a repellant or insecticidal effect against vectors of citrus greening disease. Exemplary vectors, e.g., insects, carrying the citrus greening disease include but are not limited to the psyllids *Diaphorina citri* Kuwayama and *Trioza erytreaei*. Psyllids refer to groups of phloem-feeding insects (family Psyllidae, order Homoptera) that are related to aphids, coccids, and whiteflies.

By "effective amount," amount effective," or the like as used herein, it is meant an amount effective, at dosages and for periods of time necessary to achieve the desired result, e.g., repelling or killing vectors, typically insect vectors, of citrus greening disease.

By "repelling" as used herein, it is meant that there are less vectors of citrus greening disease present in a desired area than there would have been if the action had not been taken. An infestation of vectors of citrus greening disease in a desired area is at least one vector in the desired area. Repelling also includes the prevention of an infestation by an action in desired areas where there are no pests present, but at least one pest would be present if not for the action taken.

By "killing" as used herein, it is meant the method or composition kills the vector and/or inhibits or reduces the growth of the vector. The growth of a vector has been inhibited if there has been a relative reduction in the number of vectors in a desired or predetermined area. The growth of a vector may also be said to have been inhibited if the normal growth pattern of the vector has been modified so as to have a negative effect on the individual vector. The number of vectors has been reduced by an action if there are fewer vectors in a desired area than there would have been without the action.

In accordance with one aspect of the invention, there is provided a method for killing or repelling vectors of citrus greening disease comprising exposing the vectors to an effective amount of at least one volatile compound set forth in Tables 1 and 2 (including without limitation the "unidentified" peaks) to repel or kill at least one of the vectors of citrus greening disease.

In accordance with another aspect of the present invention, there is provided a method for treating citrus plants infected with vectors of citrus greening disease comprising administering to the citrus plants or an area about the citrus plants an effective amount of at least one volatile compound set forth in Tables 1 and 2 to repel or kill at least one of the vectors of citrus greening disease.

In accordance with another aspect of the present invention, there is provided a composition comprising at least one volatile compound set forth in Tables 1 and 2 in an amount effective to repel or kill at least one vector of citrus greening disease along with an agriculturally acceptable carrier.

In accordance with another aspect of the present invention, there is provided a method of imparting, augmenting or enhancing the repellent or insecticidal effect of a composition for repelling or killing vectors of citrus greening disease by incorporating into the composition at least one volatile compound set forth in Tables 1 and 2 in an amount effective to kill or repel at least one of the vectors of citrus greening disease.

In any of the embodiments described herein, the volatile compound (active ingredient) of the present invention can be made synthetically by known methods, or can be obtained from the common guava (*Psidium guajava* L.) as set forth herein. For example, synthetic dimethyl disulfide may be provided as the volatile compound and is readily commercially available from suitable sources. Further, as set forth in the examples below, the present inventors have found that crushing guava leaves may produce greater amounts of certain sulfur and non-sulfur volatile compounds (relative to not crushing the leaves) that are believed to have a repellant or insecticidal effect on vectors of citrus greening disease. Thus, in one embodiment, the leaves of the common guava are crushed to provide one or more of the volatile compounds for use in the present invention.

Thus, in yet another aspect of the present invention there is provided a method for repelling or killing vectors of citrus greening disease. The method comprises exposing the vectors to an effective amount of a dimethyl disulfide composition to repel or kill at least one of the vectors of citrus greening disease.

In yet another aspect of the present invention, there is provided an article of manufacture. The article of manufacture comprises an amount of dimethyl disulfide effective to repel or kill at least one vector of citrus greening disease and an agriculturally acceptable carrier for the dimethyl disulfide. A container is provided that comprises the amount of dimethyl disulfide and the agriculturally acceptable carrier. The container has an integral or separate applicator for applying, e.g., spraying or the like, the contents of the container onto a desired target area. The application may be any suitable device known in the art, such as a sprayer, pump sprayer, spray nozzle, or the like.

As set forth above, the ("at least one") volatile compound for the compositions, articles of manufactures and for use in the methods set forth herein may comprise one or more compounds set forth in Table 1 and Table 2. In one embodiment, the volatile compound may be selected from the group consisting of hydrogen sulfide, methanethiol, sulfur dioxide, dimethyl sulfide (DMS), dimethyl disulfide (DMDS), methional, and dimethyl trisulfide (DTS), and combinations thereof. In a particular embodiment, the volatile compound comprises DMDS.

In an alternative embodiment, the volatile compound may instead be or may additionally comprise one or more components set forth in Table 4. In a further alternative embodiment, the volatile compound may instead be or may additionally comprise a disulfide compound selected from one of dimethyl disulfide, ethyl methyl disulfide, diethyl disulfide, methyl propyl disulfide, ethyl propyl disulfide, dipropyl disulfide, propenyl propyl disulfide, and methyl 2-propenyl disulfide. In the compositions described herein, the one or more of the volatile compounds may be provided in an amount effective to achieve the desired result, e.g., repelling or killing vectors, typically insect vectors, of citrus greening disease. For example, when the volatile compound is dimethyl disulfide, the dimethyl disulfide may be provided in a suitable agriculturally acceptable carrier, e.g., mineral oil, in a concentration of from 2 μg/ml (w/v) to 8 μg/ml, and in one embodiment 4 μg/ml (w/v) to 5 μg/ml.

In yet another aspect of the present invention, the volatile sulfur or non-sulfur compounds of the present invention may be formulated as desired and incorporated into any suitable apparatus for application onto or within the vicinity of the targeted crops. For example, the volatile sulfur or non-sulfur compounds may be prepared under pressure in a metering device.

In still another aspect of the present invention, the insecticide compositions may be applied to the subject plants by spraying the compositions on the plants, and in one embodiment, by the controlled release of the compositions. Alternatively, any other method of applying the compositions may be used. Typically, it is desirable to apply the compositions to the top and underside of the leaves of the plants, as well as an area around the trunk and root system of the plant. The composition is preferably applied to the target plants as is necessary to prevent or substantially reduce the insect population.

The amount of composition applied in any particular situation will vary depending upon a number of factors such as the nature of the crop, the level of pest infestation etc.

In addition, the compositions may be used either alone or in conjunction with other insecticides known in the art. In the latter case, the composition of the invention can lead to an improvement in performance of the other insecticide, and thus it produces an adjuvant effect. It may further reduce application rate and frequency and remediate citrus greening disease infection.

The methods, compositions, and articles of manufacture described herein are suitable for use on any tree or plant that is infected or may be infected with citrus greening disease. Exemplary plants include any cultivar from the genus *Citrus*, including but not limited to *Citrus sinensis*, lemon (*C. limon*), lime (*C. latifolia*) grapefruit (*C. paradise*), sour orange (*C. aurantium*), and mandarin (*C. reticulata*).

In addition, the insecticide compositions of the present invention are generally formed into formulations suitable for use according to a normal method for formulating agricultural/horticultural pesticides. Namely, a compound from Table 1 or 2 may be mixed with an appropriate agriculturally acceptable carrier, and if required, an auxiliary at a proper proportion, and the resultant mixture is subjected to dissolution, separation, suspension, mixing, impregnation, adsorption or adhesion and can be formulated into any desired forms for practical use, such as soluble concentrates, emulsifiable concentrates, wettable powders, water soluble powders, water dispersible granules, water soluble granules, suspension concentrates, concentrated emulsions, suspoemulsions, microemulsions, dustable powders, granules, tablets and emulsifiable gels. By "agriculturally acceptable carrier," it is meant an agent that does not have a substantial detrimental effect on the activity of the active ingredients (volatile compounds) described herein as well as the target crops.

The agriculturally acceptable carrier may be a solid, liquid, or gas. Examples of a material usable as a solid carrier include soybean flour, grain flour, wood flour, bark flour, sawing flour, tobacco stalk flour, walnut shell flour, bran, cellulose powder, a residue after plant extraction, a synthetic polymer such as a synthetic resin powder, clay (e.g., kaoline, bentonite, or acid white clay), talc (e.g., talc or pyrophyllite), silica (for example, diatomite, silica powder, mica, activated carbon, sulfur powder, pumice, calcined diatomite, brick powder, fly ash, sand, inorganic mineral powders such as calcium carbonate and calcium phosphate, chemical fertilizers such as ammonium sulfate, ammonium phosphate, ammonoium nitrate, urea, and ammonium chloride, and compost.

A suitable liquid carrier may be one having a solvent ability or a material having no solvent ability, but having an ability to assist in the dispersion of the active ingredient compound. Exemplary liquid carriers include water, alcohols (e.g., methanol, ethanol, isopropanol, butanol, and ethylene glycol); ketones (e.g., acetone, methylethyl ketone, methyl isobutyl ketone, diisobutyl ketone, and cyclohexanone); ethers (e.g., diethyl ether, dioxane, cellosolve, diisopropyl ether, and tetrahydrofuran); aliphatic hydrocarbons (e.g., kerosine and mineral oil); aromatic hydrocarbons (e.g. benzene, toluene, xylene, solvent naphtha, and alkylnaphthalene); halogenated hydrocarbons (e.g., dichloromethane, chloroform, carbon tetrachloride, and chlorobenzene); esters (e.g., ethyl acetate, butyl acetate, ethyl propionate, diisobutyl phthalate, dibutyl phthalate, and dioctyl phthalate); amides (e.g., dimethylformamide, diethylformamide, and dimethylacetamide); and nitriles (e.g., acetonitrile). In one particular embodiment, the agriculturally acceptable carrier comprises an agriculturally acceptable carrier oil, including but not limited to, mineral oil or a vegetable oil such as canola oil, sunflower oil, cottonseed oil, palm oil, soybean oil, and the like. In one further particular embodiment, mineral oil is provided as the agriculturally acceptable carrier.

When the composition will be used as an aerosol, a propellant may be added such as propane, butane, isobutane, dimethyl ether, carbon dioxide, nitrous oxide, nitrogen, and combinations thereof. Further, it is understood that the compositions of the present invention may additionally include any suitable surfactant, penetrating agent, spreading agent, thickener, anti-freezing agent, binder, anti-caking agent, disintegrating agent, anti-foaming agent, preservative, stabilizer, and the like.

EXAMPLE 1

Leaf Samples

Leaf flush from guava (*Psidium guajava* L.; Myrtaceae), two cultivars of sweet orange, *Citrus sinensis* L. Rutaceae (Hamlin and Valencia), Ray Ruby grapefruit (*C. paradisi* Macf.) and Rough lemon (*C. limon* Burm.) were harvested, weighed on Mettler® AE 160 (Greifensee, Switzerland) balance and immediately placed in 40 mL glass septum-sealed vials. Approximately 3.5 g of leaves from each plant were placed in the vial and equilibrated at room temperature for ~30 min. *Psidium guajava* and *C. limon* were obtained from Cee Jay Nursery, Lakeland, Fla. and a managed citrus grove at the Citrus Research and Education Center (CREC) in Lake Alfred, Fla., respectively, in 2007 and their seedlings have been maintained in a screenhouse since then. Seedlings of *C. sinensis* and *C. paradisi* were obtained from Southern Citrus Nurseries LLC, Dundee, Fla. in 2007. These citrus cultivars were selected for analysis because Hamlin and Valencia oranges, as well as Ray Ruby grapefruit are the most highly cultivated citrus varieties in Florida (20).

EXAMPLE 2

SPME Headspace Sampling

A 50/30 μm divinylbenzene/Carboxen/polydimethylsiloxane (DVB/Carboxen/PDMS) Stable Flex® solid phase micro extraction (SPME) fiber (Supelco, Inc., Bellefonte, Pa.) was manually inserted into a septum-sealed 40 mL glass vial for ~1 (GC-PFPD) or 15 (GC-MS) minutes to collect emanated static head space volatiles from the uncrushed guava or citrus leaf flush after it had equilibrated with ambient room conditions. Subsequently, the vial was opened to crush the leaf samples and rapidly closed to minimize volatile loss. Thereafter, the SPME fiber was again exposed to static volatiles within the vial immediately after it was closed (0 min). The vial was sampled after 10, 30 and 60 min. to investigate kinetics of volatile production from crushed leaves. Following the volatile collection, the volatile-impregnated fiber was transferred to the injector of the GC-PFPD or GC-MS and desorbed for ~5 min at 200° C. (for the ZB-5 column) and 240° C. (for the DB-wax column). (See Example 3 for discussion of the columns used below).

EXAMPLE 3

GC-Pulse Flame Photometric Detector, PFPD

Sulfur-compounds were analyzed using a Pulsed Flame Photometric Detector (PFPD) (Model 5380, OI Analytical Co., College Station, Tex.) set up in the sulfur mode coupled to a HP-5890 Series II GC Separation. Tentative identification was accomplished using three different capillary columns: (a) ZB-5 (30 m×0.32 mm. i.d.×0.5 μm, (Zebron ZB-5, Phenomenex, Inc., Torrance, Calif.); (b) DB-wax (30 m×0.32 mm. i.d.×0.5 μm, J&W Scientific Inc.; Folsom, Calif.); and (c) a Gas Pro PLOT column (30 m×0.32 mm. i.d., Agilent Technologies Inc., Palo Alto, Calif.). The ZB-5 column oven temperature was programmed from 40 to 265° C. and from 40 to 240° C. for DB-wax at 7° C./min, with a 5 min hold at the maximum temperature. Helium was used as carrier gas at flow rate of 1.5 mL/min. Injector and detector temperature were 200° C. and 250° C. respectively. A 0.75 mm injector liner was employed to improve peak shape and chromatographic efficiency. Injections were splitless. Identification of sulfur volatiles was determined by matching the Linear Retention Index (LRI) values with authentic standards on both polar and non polar columns. LRI values are based on retention times of an n-alkane standard measured on the same column as the compounds of interest. LRI values depend only on the type of stationary phase used (e.g. polymethylsiloxanes, wax etc.), and are independent of the column dimensions.

EXAMPLE 4

GC-MS

Analyses were performed with a PerkinElmer Glarus 500 quadrupole mass spectrometer equipped with TurboMass software (Perkin Elmer Las Inc., Shelton, Conn.) and a RTX-5 capillary column (Restek Corp., Bellafonte, Pa.); 60 m×0.25 mm. i.d.×0.50 μm). Helium was used as the carrier gas in the constant flow mode of 2 mL/min. The source was kept at 200° C., and the transfer line and injector were maintained at 260° C. The oven temperature program consisted of a linear gradient from 40° C. to 260° C. at 7° C./min. Electron impact ionization in the positive ion mode was used (70 eV), either scanning a mass range from 25-300 m/z or acquiring data in the selected ion mode. Mass spectra matches were made by comparison of NIST 2005 version 2.0 standard spectra (NIST, Gaithersburg, Md.). Only those compounds with spectral fit values equal to or greater than 800 and appropriate LRI values were considered positive identifications. Authentic standards were used to confirm identifications when ever available.

EXAMPLE 5

Identification of Sulfur Volatiles

As shown in Table 1 below, the preliminary identifications of the seven identified guava leaf sulfur volatiles was based on matching standardized retention index values from three dissimilar columns with those of authentic standards. These values were obtained using the pulsed flame photometric detector, which is highly selective for detecting sulfur volatiles only. On some column types, the sulfur volatiles are not sufficiently different to provide unambiguous identification. However, when using the LRI values from all three columns a unique set of values can be determined for unambiguous identification. Even the relative elution order is different on some columns as exemplified by methional and dimethyl trisulfide on ZB-5 and DB-wax columns. This provides additional unique information in terms of peak identification. On the other hand, hydrogen sulfide is the first peak in all three chromatographic systems. Although hydrogen sulfide's retention time is very close to that of methanethiol on a ZB-5 column, it is well resolved on both wax and PLOT columns. Furthermore, methanethiol is not resolved from sulfur dioxide on the PLOT column and is only slightly resolved on the ZB-5 column, but is well resolved on the wax column. Methional and dimethyl trisulfide values were not obtained for the PLOT column as they were too highly retained and were not required as ZB-5 and wax LRI values were sufficiently unique so as to provide satisfactory identification.

Table 1—Linear Retention Index, LRI, values of guava sulfur volatiles on three dissimilar columns. Sulfur volatiles denoted with an asterisk(*), were only observed from crushed guava leaves.

TABLE 1

| Sulfur Volatile | Linear Retention Index Values | | |
| --- | --- | --- | --- |
| | ZB-5 | Wax | PLOT |
| Hydrogen sulfide | <500 | 528 | <400 |
| Methanethiol | <500 | 675 | 414 |
| sulfur dioxide | <500 | 831 | 414 |
| dimethyl sulfide, DMS | 519 | 736 | 718 |
| dimethyl disulfide, DMDS* | 744 | 1064 | 860 |
| Methional | 914 | 1450 | |
| dimethyl trisulfide, DMTS* | 978 | 1355 | |

EXAMPLE 6

Sulfur Volatiles in Crushed and Intact Guava Leaves

Figure 1:
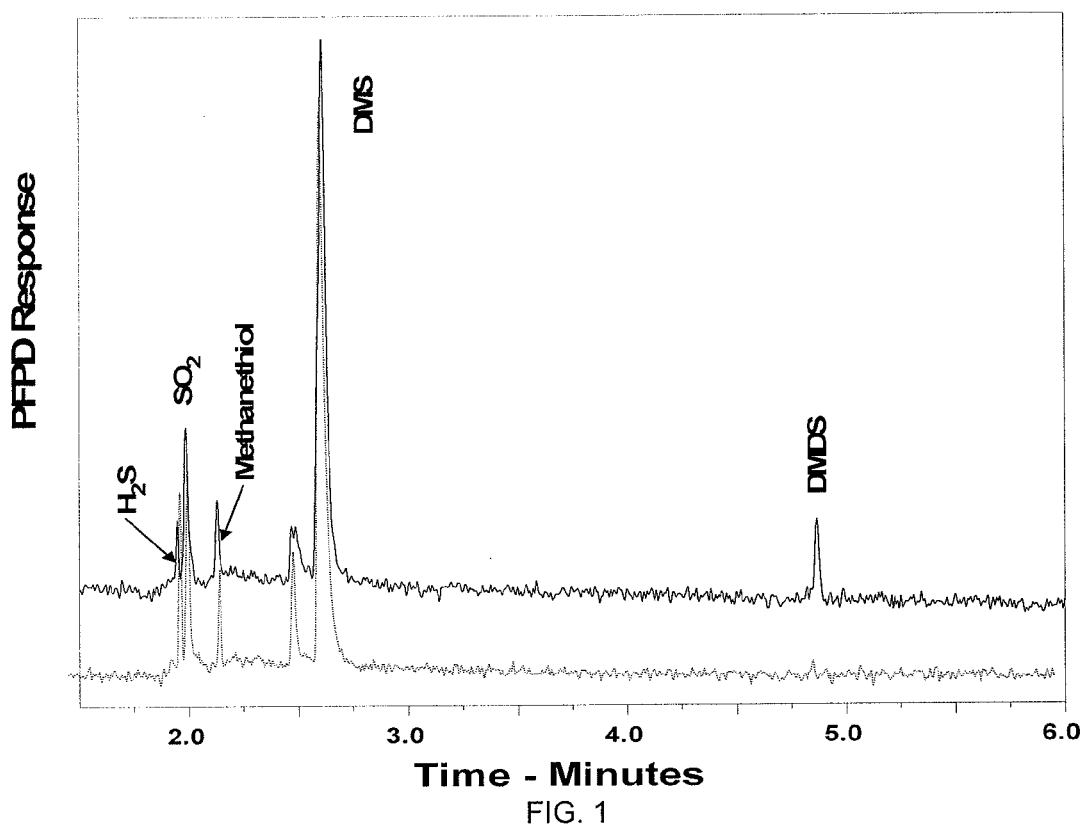
FIG. 1 is a comparison of sulfur chromatograms from intact (lower trace) and crushed (upper trace) guava leaves.

As shown in the lower sulfur chromatogram in FIG. 1, there are five sulfur volatiles in undamaged guava leaves. It should be pointed out that the sulfur chromatograms were obtained using a PFPD detector in the sulfur (square root mode) that is both highly selective and sensitive for sulfur volatiles. The output from the same sample detected using the PFPD carbon mode is much more complex. The sulfur volatiles have been identified as: hydrogen sulfide, sulfur dioxide, methanethiol and dimethyl sulfide. The small peak between methanethiol and dimethyl sulfide is unidentified at the present time. The upper chromatogram shows the sulfur volatiles produced immediately after the leaves are crushed. This chromatogram contains all of the previously identified sulfur volatiles, plus dimethyl disulfide (DMDS). Also produced as a result of crushing, but not shown, are methional and traces of dimethyl trisulfide.

EXAMPLE 7

Sulfur Volatiles in Crushed and Intact Citrus Leaves

Since citrus leaves are highly susceptible to psyllid attack and guava leaves seem to induce a repellent effect, the volatile(s) responsible for the repellency are present only in the guava leaves. Therefore, citrus leaves were crushed and analyzed in the same manner as the guava leaves. The leaves from four different citrus cultivars were evaluated for sulfur volatiles. Evaluated cultivars included both Valencia and Hamlin sweet orange (Citrus sinensis), lemon (C. limon), lime (C. latifolia) grapefruit (C. paradise), sour orange (C. aurantium), and mandarin (C. reticulata). All of the citrus leaves produced dimethyl sulfide at low levels in uncrushed leaves and the relative concentration of dimethyl sulfide increased over tenfold when the leaves were crushed. Although the injury response elevated concentrations of dimethyl sulfide, dimethyl disulfide was not produced in any of the citrus cultivars evaluated either wounded or unwounded. Therefore, citrus leaves lack the ability to produce the potent defensive chemical dimethyl disulfide (DMDS), which is believed to explain, in part, guava's unique repellent properties, which are not shared with citrus.

EXAMPLE 8

Formation Kinetics of Dimethyl Disulfide in Crushed Guava Leaves

Figure 2:
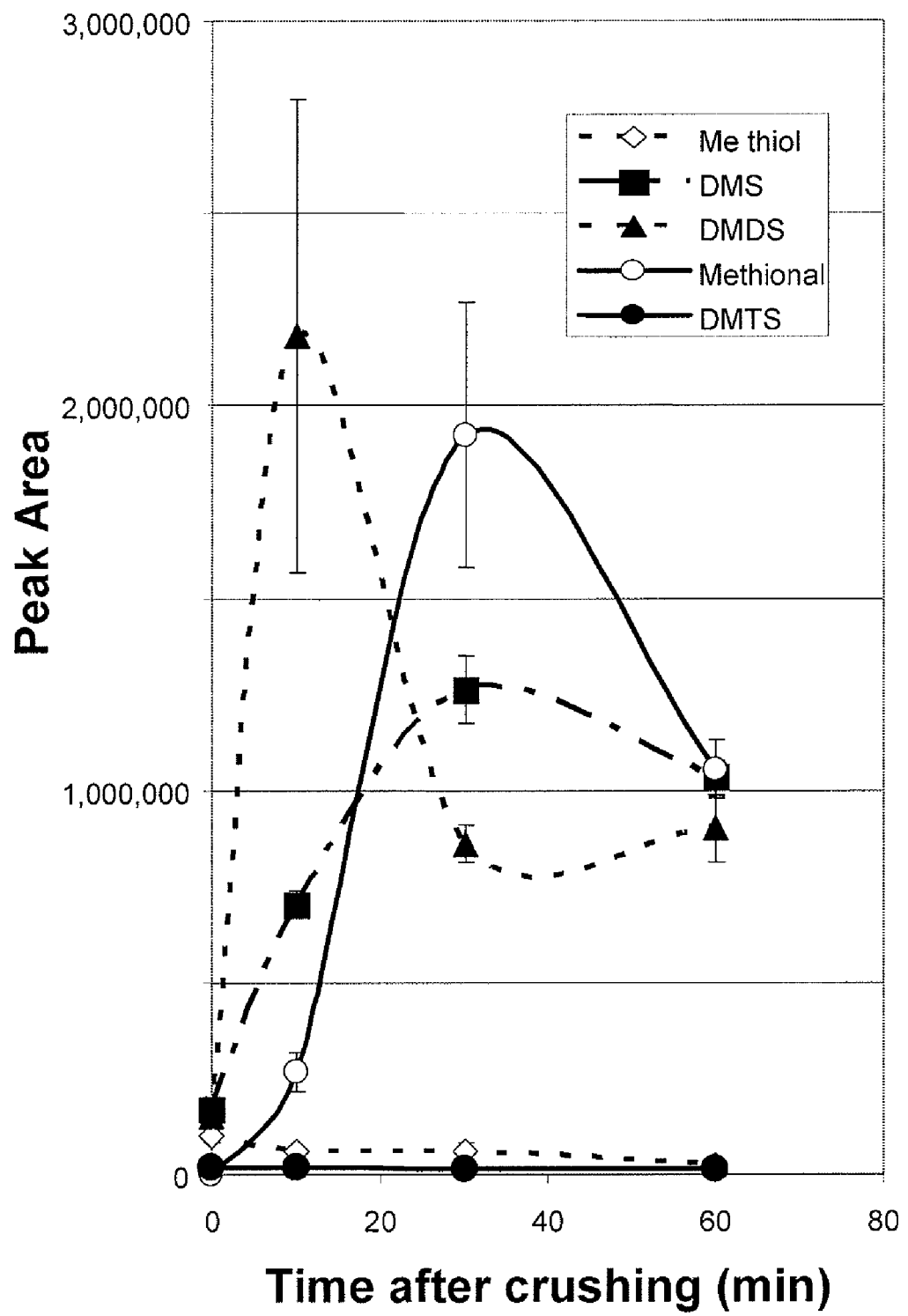
FIG. 2 is a graph showing the change in guava leaf volatile peak areas after crushing of the guava leaves.

As shown in FIG. 2, dimethyl disulfide is formed rapidly once guava leaves are crushed. In particular, DMDS becomes the most prominent static headspace volatile within 10 minutes after crushing, but then its concentration diminishes just as rapidly as it was formed—presumably due to the conversion to dimethyl trisulfide. Methional and dimethyl sulfide also increase, but not as rapidly as DMDS, reaching maximum concentrations at about 25 min after crushing and then slowly diminishing thereafter. For this reason, it may be desirable to control the release of applications of compositions comprising DMDS such that DMDS is administered repeatedly to the targeted plants over a period of time.

EXAMPLE 9

GC-MS Identification of Guava Leaf Volatiles

Figure 3:
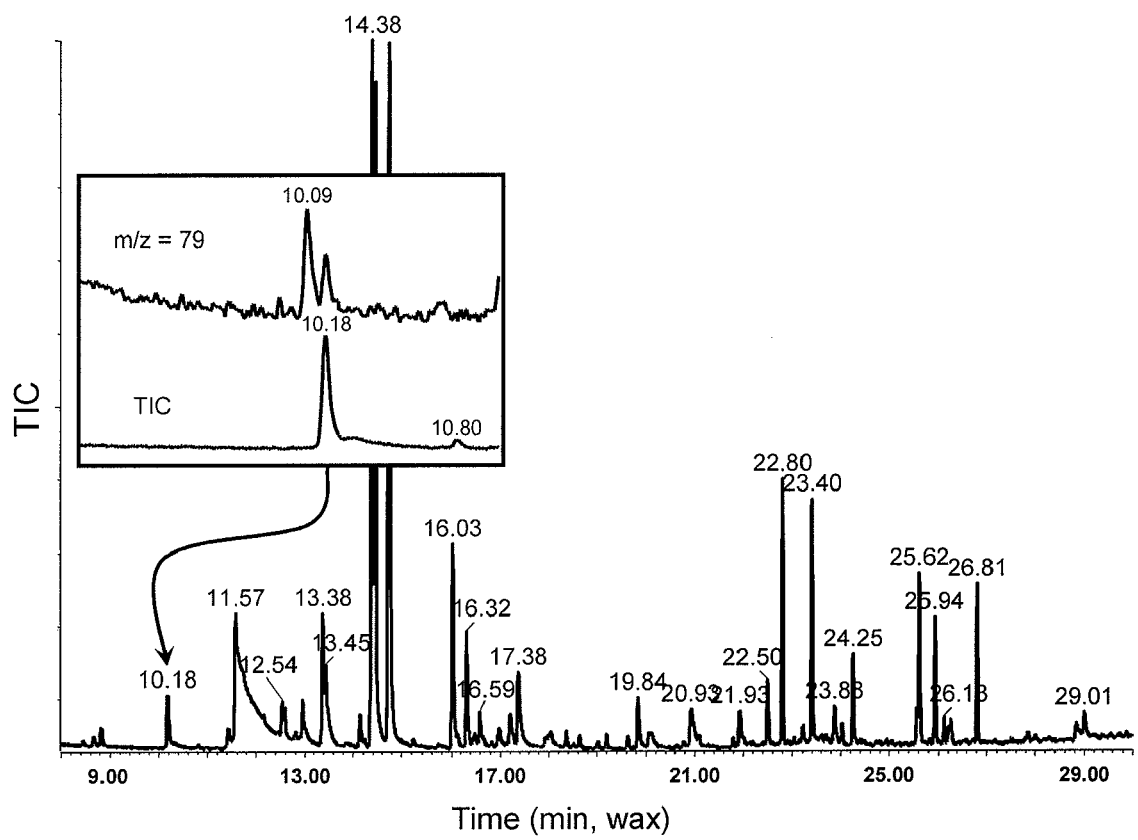
FIG. 3 is a Total Ion Current (TIC) chromatogram from a sample of crushed guava leaves.

The Total Ion Current (TIC) chromatogram from fresh, new growth, and crushed guava leaves at room temperature is shown in FIG. 3 and the corresponding peak identifications are shown in Table 2 (below). Forty-eight sulfur and non-sulfur volatiles are identified. Over 100 peaks were observed in the high resolution capillary chromatogram, but only the 50 largest peaks are included in Table 2. These 50 peaks account for 92% of the total peak area whereas the remaining peaks comprised only 8% of the remaining total peak area. As one might expect in complex samples such as guava volatiles, there is some coelution. It can be seen from Table 2 that the front half of the peak at 8.67 min is comprised of methyl 3-methylbutyrate and the back portion is comprised of α-pinene. α-Copaene, which was found in the crushed guava leaves in this study at 19.01 min, has also been reported to be a component in guava fruit (8, 22) and is a reported attractant to the Mediterranean fruit fly, Ceratitis capitata (23). α-Copaene is also found in citrus. As also can be seen in Table 2, the major guava headspace volatiles are comprised of esters; isoamyl 3-methylbutyrate (19.33%), isoamyl 2-methylbutyrate (10.68%), 2-methylbutyl 2-methylbutyrate (8.21%) and aldehydes; Z-3-hexenal, 14.6%.

DMDS can be detected using MS in the extracted ion mode using m/z 79 (corresponding to $CH_3S_2+$, DMDS minus methyl group) as shown for the peak at 10.09 min. in the insert in FIG. 3. DMDS also has a strong M+ ion at m/z 94, but cannot be used for quantitation as another compound with a fragment at this same m/z elutes on the back half of the DMDS peak. It is not readily observed in the TIC mode, although with proper background subtraction a confirming fragmentation pattern can be obtained with match value of 801 and a reverse match of 875. Standard DMDS also elutes at 10.09 min.

TABLE 2

GC-MS Identifications from total ion chromatograms. Values in ( ) indicate goodness of fit on the basis of 1,000 for a perfect fit.
RT = retention time.

| Rt | Obs LRI | Ref. LRI | % | Name (fit) | CAS No. |
|---|---|---|---|---|---|
| 7.2 | 970 | 969 | 0.08 | 2-ethylfuran (926) | 3208-16-0 |
| 7.8 | 997 | 996 | 0.08 | 3-pentanone (879) | 99-22-0 |
| 8.4 | 1025 | 1024 | 0.09 | methyl 2-methylbutyrate (919) | 868-57-5 |
| 8.6 | 1035 | 1034 | 0.23 | methyl 3-methylbutyrate (880) | 556-24-1 |
| | | 1038 | — | /α-pinene (925) | 7785-70-8 |
| 8.8 | 1041 | 1040 | 0.36 | ethyl vinyl ketone (927) | 1629-58-9 |
| 10.1 | 1101 | 1101 | 1.15 | hexanal (939) | 66-25-1 |
| 10.8 | 1129 | 1131 | 0.1 | E-2-pentenal (897) | 1576-87-0 |
| 11.5 | 1163 | 1151 | 14.55 | Z-3-hexenal (880) | 6789-80-6 |
| 12.1 | 1189 | | 1.16 | isobutyl 2-methylbutyrate (916) | 2445-67-2 |
| 12.4 | 1203 | 1202 | 0.05 | isobutyl 3-methylbutyrate (850) | 589-59-3 |
| 12.5 | 1207 | 1206 | 0.54 | isoamyl butyrate | 106-27-4 |
| 12.5 | 1209 | 1208 | 0.56 | isoamyl isobutyrate | 2050-01-3 |
| 12.8 | 1219 | 1220 | 0.14 | limonene (927) | 138-86-3 |
| 13.3 | 1245 | 1236 | 2.41 | E-2-hexenal (940) | 6728-26-3 |
| 13.4 | 1248 | 1249 | 2.88 | (Z)-β-ocimene (897) | 3338-55-4 |
| 14.1 | 1281 | | 0.67 | amyl butyrate (938) | 540-18-1 |
| 14.3 | 1293 | 1276 | 10.68 | isoamyl 2-methylbutyrate (962) | 27625-35-0 |
| 14.4 | 1296 | 1294 | 8.21 | 2-methylbutyl 2-methylbutyrate (951) | 2445-78-5 |
| 14.7 | 1310 | 1308 | 19.33 | isoamyl 3-methylbutyrate (917) | 659-70-1 |
| 15.2 | 1334 | 1334 | 0.15 | Z-2-pentenol (838) | 1576-95-0 |
| 16.0 | 1373 | | 3.95 | Unidentified | |
| 16.3 | 1388 | | 2.1 | 3-methyl-3-butenyl 3-methylbutyrate (948) | 54410-94-5 |
| 16.5 | 1401 | 1400 | 0.64 | Z-3-hexenol (924) | 928-96-1 |
| 16.9 | 1421 | 1419 | 0.54 | neo-allo-ocimene (909) | 673-84-7 |
| 17.2 | 1432 | | 0.78 | (E,Z)-2,4-hexadienal (931) | 53398-76-8 |
| 17.3 | 1441 | 1440 | 2.45 | (E,E)-2,4-hexadienal (927) | 142-83-6 |
| 17.9 | 1471 | 1469 | 0.25 | α-p-dimethylstyrene (949) | 1195-32-0 |
| 18.3 | 1492 | 1492 | 0.29 | Z-3-hexenyl 2-methylbutyrate (930) | 53398-85-9 |
| 18.5 | 1501 | 1500 | 0.07 | pentadecane (869) | 629-62-9 |
| 18.6 | 1508 | 1507 | 0.23 | Z-3-hexenyl 3-methylbutyrate (927) | 35154-45-1 |
| 19.0 | 1527 | | 0.14 | α-copaene (908) | 3856-25-5 |
| 19.6 | 1560 | 1560 | 0.27 | cyclohexyl 3-methylbutyrate (894) | 7774-44-9 |
| 19.8 | 1572 | 1571 | 1.11 | benzaldehyde (968) | 100-52-7 |
| 20.7 | 1623 | 1600 | 0.12 | β-elemene (922) | 515-13-9 |
| 20.9 | 1632 | | 1.67 | Unidentified | |
| 21.0 | 1641 | 1641 | 0.3 | β-caryophyllene (913) | 87-44-5 |
| 21.8 | 1681 | 1666 | 0.16 | β-farnesene (890) | 18794-84-8 |
| 21.9 | 1689 | 1690 | 1.05 | 3-methylbutyric acid (882) | 503-74-2 |
| 22.5 | 1722 | | 1.14 | methyl geranate (928) | 2349-14-6 |
| 22.8 | 1740 | 1745 | 4.16 | (Z,E)-α-farnesene (931) | 26560-14-5 |
| 23.0 | 1755 | 1753 | 0.12 | β-bisabolene (913) | 495-61-4 |
| 23.2 | 1765 | 1765 | 0.32 | (E,E)-α-farnesene (925) | 502-61-4 |
| 23.4 | 1776 | 1767 | 4.14 | geranyl acetate (955) | 105-87-3 |
| 23.8 | 1804 | | 0.84 | curcumene (912) | 644-30-4 |
| 24.0 | 1814 | | 0.31 | 5-ethyl-2(5H)-furanone (927) | 2407-43-4 |
| 24.2 | 1828 | 1837 | 1.7 | geranyl propionate (913) | 105-90-8 |
| 25.6 | 1915 | 1912 | 2.92 | geranyl butyrate (944) | 106-29-6 |
| 25.9 | 1936 | | 2.12 | geranyl isovalerate (947) | 109-20-6 |
| 26.2 | 1958 | 1957 | 0.44 | isoamyl benzoate (909) | 94-46-2 |
| 26.8 | 1994 | | 2.24 | Unidentified | |

The following examples (from Example 10 on) investigate the effect of guava leaf volatiles on *D. citri*'s behavioral response to citrus volatiles. In addition, the effect of authentic guava leaf volatiles on *D. citri* behavior was compared with that of synthetic DMDS. The following examples further establish that a synthetic guava-based repellant would be useful for the treatment of plants infected with citrus greening disease.

EXAMPLE 10

Insects and Leaf Samples

Adult *D. citri* used for the behavioral bioassays were drawn from a continuously reared culture at the University of Florida Citrus Research and Education Center (Lake Alfred, USA) and established in 2000 from field populations in Polk Co., FL, USA (28.0'N, 81.9'W) prior to the discovery of citrus greening disease in FL. This culture is maintained on sour orange (*Citrus aurantium* L.) and 'Hamlin' orange [*C. sinensis* (L.)] seedlings at 27±1° C., 63±2% RH, and L14:D10 photoperiod. Freshly emerged unsexed adult psyllids were first placed on citrus seedlings in Plexiglass cages for up to 7 d for sexual maturation prior to use in experiments.

Secondary plant metabolites are typically not evenly distributed within plants (Loomis & Croteau, 1980). In order to maximize the amount of static volatile metabolites for analyses, we used fresh leaf flush [immature leaves at the growing shoots (Hall & Albrigo, 2007)], which are known to contain a higher proportion of plant metabolites (Hruitfiord et al., 1974) compared with older leaves or other plant parts. Headspace volatiles were collected from leaf flush of 'white' guava (*Psidium guajava* L.; Myrtaceae) or sweet (Hamlin) orange, *Citrus sinensis* L. Rutaceae using a static solid phase micro extraction (SPME) technique similar to that described in Rouseff R L, Onagbola E O, Smoot J M & Stelinski L L (2008) Sulfur volatiles in guava (*Psidium guajava* L.) leaves: possible defense mechanism. Journal of Agricultural and Food Chemistry 56: 8905-8910. (Rouseff et al. (2008)), the entirety of which is hereby incorporated by reference. Leaf flush from guava and citrus was harvested and weighed on a Mettler® AE 160 balance (Greifensee, Switzerland). Approximately 3.5 g of guava or citrus leaves was weighed into 40 mL septum-sealed glass vials, which were allowed to equilibrate at ambient laboratory conditions for ~30 min. Accumulated static head-space volatiles were collected from the glass vials at 0, 10, 30 and 60 min post exposure to ambient laboratory conditions. Static head-space volatiles were collected using a 75 μm Carboxen-polydimethylsiloxane (PDMS) Stable Flex® SPME fiber (Supelco, Inc., Bellefonte, Pa.). At least three replicates of each static volatile sample were analyzed.

Husbandry methods for the 'white' guava and 'Hamlin' citrus plants used in these investigations have been described previously (Rouseff et al., 2008). 'Hamlin' citrus was selected for analysis because it is one of the most highly cultivated citrus varieties in Florida. Half of the samples were gently crushed (using a clean glass rod) to simulate plant damage and the remaining half were not crushed. All samples (~3.5 g leaf flush/sample) were wrapped in Kim wipes (Kimberly-Clark®, Ontario, Canada) and placed in 2.5 cm×12.5 cm extending glass tubes of a 4-choice olfactometer [Analytical Research Systems, ARS (Gainesville, Fla.)], for behavioral investigations described below.

EXAMPLE 11

Four-Choice Olfactometer Test

Behavioral responses of *D. citri* to citrus volatiles with or without guava or DMDS volatiles were quantified using a 4-choice olfactometer (Analytical Research Systems, Inc. (ARS), Gainesville, Fla., USA) based on the design of Pettersson (1970), Vet et al. (1983) and Kalule & Wright (2004). The olfactometer consists of a 5 cm×30 cm×30 cm stage on four 2.5 cm×15 cm legs with extending orifices on four sides of the stage. Charcoal-purified and humidified air was drawn through these arms via a vacuum pump creating four potential odor fields. Air pulled through the olfactometer was evacuated through a central orifice on the floor of the stage. During each experimental run, two of the four orifices on the sides of the stage were designated for odor stimuli treatments and the two others were left as blank. The clean air negative control consisted of charcoal-filtered, purified, and humidified laboratory air in all four arms of the olfactometer, while the host plant positive control consisted of two arms loaded with citrus leaves and two arms left blank. The effect of repellent chemicals was measured by adding guava leaves or a formulation of synthetic DMDS to citrus flush in two arms of the olfactometer as described below. The orifices of the olfactometer were connected through Teflon®-lined glass tube (ARS, Gainesville, Fla.), connectors to four pumps on an air delivery system (ADS) equipped with a vacuum pump (ARS, Gainesville, Fla.), which suctioned air out of the olfactometer through a central orifice. A constant airflow of 0.1 L/min was maintained through each of the four orifices and a 0.5 L/min suction flow was maintained to vacuum the odor mixture from the olfactometer. Two fluorescent lights (~250 lux) were positioned centrally above the olfactometer, which were housed within a 76 cm×81 cm×86 cm white fiber board box for uniform light diffusion. A second 25 cm×30 cm×30 cm box, whose inside walls and roof were lined with black cloth, was placed directly over the olfactometer to completely shield the stage of the olfactometer from light, but not the traps and the extending arms.

The behavioral response of adult *D. citri* to clean laboratory air was first investigated to 4 blank arms of the olfactometer as a negative control to ensure no positional bias. Thereafter, *D. citri* response was measured to citrus leaf volatiles with and without volatiles from guava leaves or synthetic DMDS. For each olfactory treatment combination, two of the olfactometer arms were randomly designated for volatiles and the other two were left blank receiving charcoal-filtered, purified, and humidified laboratory air only. Eight treatments were compared, which are summarized in Table 3 below. Ten *D. citri* were assayed per replicate that lasted 1.5 h. Stimuli sources were placed in opposite or adjacent positions with respect to one another and rotated twice after each run.

In treatments investigating synthetic dimethyl disulfide (DMDS) (Sigma-Aldrich Inc., USA), 100 μL of a 4.3 μg/μL (w/v) solution of DMDS in mineral oil (Sigma-Aldrich Inc., USA) was pipetted onto a 1 cm×1 cm braided piece of Richmond cotton wick (Petty John Packaging, Inc. Concord, N.C.) to slow release rate (Arthur, 1996; Dugravot et al., 2002). The DMDS was mixed with mineral to reduce release during bioassays given its high volatility (Dugravot et al., 2004). This dosage was selected based on a preliminary investigation showing it to optimally repel adult *D. citri*, compared with lower dosages tested on a log scale (data not shown).

After every run, the olfactometer as well as the glass tubes were first washed in soapy water and rinsed with distilled water. The glass tubes were then rinsed with acetone and the olfactometer stage (made of Plexiglass and Teflon®) was cleaned with absolute alcohol. Thereafter, the olfactometer was air dried. Each experiment was replicated at least 15 times resulting in a total of at least 150 *D. citri* assayed per treatment concentration. All observations were made at 25±1° C., 60±5% r.h. under an incandescent light of ~250 lux.

TABLE 3

Summary of odor combinations for each treatment in 4-choice olfactometer.

| Experiments | Olfactometer arm | | | | t |
|---|---|---|---|---|---|
| | 1 | 2 | 3 | 4 | |
| 1 | Laboratory air | Laboratory air | Intact citrus | Intact citrus | −3.63 |
| 2 | Laboratory air | Laboratory air | Intact citrus | DMDS | 3.05 |
| 3 | Laboratory air | Laboratory air | Crushed citrus | DMDS | 7.23 |
| 4 | Laboratory air | Laboratory air | Mineral oil | DMDS | 6.25 |
| 5 | Laboratory air | Laboratory air | Crushed guava | Crushed citrus | 7.89 |
| 6 | Laboratory air | Laboratory air | Intact guava | Intact citrus | 3.21 |
| 7 | Laboratory air | Laboratory air | Crushed guava | Intact guava | 4.80 |
| 8 | Laboratory air | Laboratory air | Crushed citrus | Intact citrus | −0.51 |

't' values were obtained comparing the percentages of repelled versus attracted *D. citri* using student's t-test (P < 0.05).

When presented with clean air, *D. citri* responded equally to each of the four arms of the olfactometer (F=0.79, d.f.=4, P=0.534), indicating no positional bias in the bioassays. Specifically, 20, 19, 22, and 16% of the tested psyllids (n=200) oriented to each of the four extending arms of the olfactometer while nearly 24% remained in the central orifice insertion point. Significantly (F=15.19, d.f.=7, P<0.0001) more *D. citri* were repelled in treatments in which intact guava, crushed guava, or DMDS were co-presented with citrus than when intact or crushed citrus alone was presented (FIG. 5). The percentage of *D. citri* not moving from the central orifice ranged between 62 and 75% when guava or DMDS were presented with citrus compared 32 to 48% when citrus alone was presented (FIG. 5).

In general, significantly (Student's t-test, =−3.63, d.f.=1, P=0.001) more *D. citri* oriented to intact citrus than clean air (Table 3). However, *D. citri* were not significantly (Table 3; t=−0.51, d.f.=1, P=0.610) attracted to the combination of intact and crushed citrus volatiles (FIG. 5). Both intact and crushed guava leaves significantly (t=4.80, d.f.=1, P<0.0001) repelled *D. citri*'s response in the olfactometer (Table 3). Approximately 71% of the 210 *D. citri* tested did not move from the release point. When volatiles from intact (Table 3; t=3.21, d.f.=1, P=0.003) or crushed (Table 1; t=7.89, d.f.=1, P<0.0001) guava were co-released with citrus, significantly fewer *D. citri* were found in the extending arms of the olfactometer than at the release point (FIG. 5). Significantly (Table 3; t=6.25, d.f.=1, P<0.0001) more *D. citri* were found at the insertion point of the olfactometer than in the extending arms when psyllids were exposed to synthetic DMDS. Significantly (Table 3; t=3.05, d.f.=1, P=0.004) more *D. citri* were also repelled when DMDS was co-released with intact citrus volatiles.

EXAMPLE 12

Gas Chromatography-Pulse Flame Photometric Detector (GC-PFPD) Analyses

Methods used for volatile analyses in this study are similar to those described in Rouseff et al. (2008). Sulfur-compounds were analyzed using a pulsed flame photometric detector (PFPD) (Model 5380, OI Analytical Co., College Station, Tex., USA) set up in the sulfur mode coupled to a HP-5890 Series II GC. The PFPD specifically detects presence of sulfur and carbon in volatile samples. The GC was equipped with a 30 m×0.32 mm. i.d.×0.5 µm ZB-5 (Zebron ZB-5, Phenomenex, Inc. Torrance, Calif., USA) capillary column and programmed from 40 to 265° C. at 7° C./min, with a 5 min hold at the maximum temperature. Helium was used as carrier gas at a flow rate of 1.5 mL/min and set injector and detector temperatures at 200° C. and 250° C., respectively. The GC was operated in splitless mode and sulfur volatiles were identified by matching the Linear Retention Index, LRI, values with authentic standards (Rouseff et al., 2008).

The above pulsed flame photometric detector (PFPD) analyses of static head-space volatiles revealed the presence of carbon-disulfide ($CS_2$) in intact (non-crushed) samples of both guava and citrus. Dimethyl sulfide (DMS) was also released by intact citrus flush. Gentle crushing of leaf samples resulted in a significant immediate reduction in $CS_2$ production in both guava and citrus, but triggered an escalated increase in production of DMS in guava (FIG. 4). The amount of DMS produced by the crushed citrus flush was relatively small at first, but increased over time (FIG. 4). In addition, methanethiol ($CH_3SH$) and dimethyl disulfide (DMDS) were produced by crushed guava leaves in appreciable quantities (FIG. 4).

EXAMPLE 13

Gas Chromatography-Mass Spectrometry (GC-MS) Analyses

In the preceding 4-choice olfactometer experiment, when volatiles from intact guava and intact citrus were being tested, it was observed that some of the *D. citri* that were captured in the glass trap laid motionless on their back. Therefore, we collected samples from the mixed intact guava and intact citrus volatiles for GC-MS analyses. The mixture of volatiles expelled from the central orifice of the 4-choice olfactometer was pumped through a volatile collection chamber (VCC) (ARS, Gainesville, Fla., USA) connected to the olfactometer with Teflon® tubes. A 75 µm Carboxen—PDMS SPME fiber was inserted into the VCC to collect volatile samples emanating from intact guava and intact citrus for ~1.5 h. In addition, static head-space volatiles were separately collected from ~3.5 g samples of intact guava and citrus flush for GC-MS analyses following methods described previously by Rouseff et al. (2008). At least three replicates of each volatile sample were analyzed.

The collected volatiles were analyzed and identified with a coupled Perkin/Elmer® Glarus 500 quadrupole gas chromatograph coupled to mass spectrometer (GC-MS). The GC-MS was equipped with Turbo Mass software (PerkinElmer, Inc., Shelton, Conn.) and a 60 m×0.25 mm, i.d.×0.50 µm Restek (RTX-5) capillary column. Helium was used as the carrier gas in the constant flow mode of 2 mL/min. The source was kept at 200° C., and the transfer line and injector were maintained at 260° C. The oven was programmed from 40° C. to 260° C. at 7° C./min. Mass spectra were matched with NIST 2005 version 2.0 standard spectra (NIST, Gaithersburg, Md.) and compounds with spectral fit values equal to or greater than 800 and appropriate LRI values were considered positive identifications. Authentic standards were used to confirm identifications when available. Thereafter, the identified volatiles from intact guava and citrus were compared.

Table 4 shows the various compounds obtained by the GC-MS analyses from the combination of intact guava and intact citrus during the 4-choice olfactometer bioassays. Nine guava-specific compounds were identified including: acetic acid (3.8%), benzaldehyde (1.7%), (Z)-3-hexenal (1.5%) and (Z)-3-hexenyl acetate (4.1%). There were fifteen citrus-specific volatiles including dl-limonene, sabinene, α-terpinolene and τ-terpene and they constituted approximately 8.1, 13.6, 2.4 and 3.4% of the total volatile blend. Alloocimene, (Z)-3-hexen-1-ol, ethanol, (E)-caryophyllene, α-copaene and β-myrcene were among fifteen volatiles common to leaf flushes of both plant types (Table 2).

EXAMPLE 14

Y-Tube Olfactometer Test

In order to confirm the repellent effect of synthetic DMDS against *D. citri*, an additional study using a Y-tube olfactometer (ARS, Gainesville, Fla., USA) was conducted. The Y-tube consisted of a central stem (13.5 cm long, 2.4 cm o.d.) with two lateral arms (5.75 cm long, 2.4 cm o.d.). The lateral arms were connected to extending glass tubes (14.5 cm long, 1.9 cm o.d.) with inlayed sieves (5.25 cm away from connection) to prevent insect escape and serve as an end point of the lateral arms. Charcoal-filtered laboratory air was passed from an air pump, into each of the extending arms of the olfactometer at a rate 100 mL/min. The Y-tube was suspended vertically on a clear plexiglass plate and placed in the white fiberboard box described above, for uniform light diffusion and to minimize visual distraction of the adult *D. citri*.

Two Y-tube experiments were conducted to further investigate the repellent effect of the DMDS against the attractiveness of citrus volatiles to *D. citri*. In the first experiment, a mixture of volatiles from 100 µL of the DMDS solution in mineral oil described above and ~3.5 g citrus flush were

TABLE 4

Volatile compounds identified from GC-MS analyses of intact citrus and guava volatiles

| Group | S/N | RT | Compound | MW | CAS # | LRI | % |
|---|---|---|---|---|---|---|---|
| Guava | 1 | 7.84 | 3-Pentanone | 86 | 96-22-0 | 998 | 0.91 |
| | 2 | 17.98 | Acetic acid | 60 | 64-19-7 | 1474 | 3.80 |
| | 3 | 19.83 | Benzaldehyde | 106 | 100-52-7 | 1573 | 1.68 |
| | 4 | 11.57 | (Z)-3-hexenal | 98 | 6789-80-6 | 1163 | 1.50 |
| | 5 | 15.27 | (Z)-3-hexenyl acetate | 142 | 3681-71-8 | 1336 | 4.07 |
| | 6 | 24.80 | Hexanoic acid | 116 | 142-62-1 | 1864 | 0.26 |
| | 7 | 27.46 | Phenol | 94 | 108-95-2 | 2041 | 0.42 |
| | 8 | 25.20 | Triethylene glycol | 150 | 112-27-6 | 1890 | 0.06 |
| | 9 | 19.76 | α-Gurjunene | 204 | 489-40-7 | 1569 | 0.18 |
| Citrus | 1 | 14.19 | dl-Limonene | 136 | 138-86-3 | 1040 | 8.07 |
| | 2 | 14.03 | Cymene | 134 | 535-77-3 | 1035 | 1.72 |
| | 3 | 12.87 | Sabinene | 136 | 3387-41-5 | 984 | 13.62 |
| | 4 | 11.60 | Thujenene | 136 | 58037-87-9 | 936 | 1.36 |
| | 5 | 15.79 | (E)-Sabinene hydrate | 154 | 17699-16-0 | 1114 | 1.13 |
| | 6 | 21.19 | α-Cucubene | 204 | 17699-14-8 | 1373 | 0.02 |
| | 7 | 13.55 | α-Phellandrene | 136 | 99-83-2 | 1017 | 1.21 |
| | 8 | 11.85 | α-Pinene | 136 | 80-56-8 | 947 | 0.26 |
| | 9 | 13.83 | α-Terpinene | 136 | 99-86-5 | 1029 | 0.31 |
| | 10 | 17.88 | α-Terpineol | 154 | 98-55-5 | 12.10 | 0.57 |
| | 11 | 15.45 | α-Terpinolene | 136 | 586-62-9 | 1099 | 2.35 |
| | 12 | 21.90 | β-Elemene | 204 | 515-13-9 | 1410 | 0.18 |
| | 13 | 24.04 | β-Selinene | 204 | 17066-67-0 | 1528 | 0.04 |
| | 14 | 13.75 | δ-3-Carene | 136 | 13466-78-9 | 1022 | 0.93 |
| | 15 | 14.80 | τ-Terpinene | 136 | 99-85-4 | 1070 | 3.42 |
| Both | 1 | 22.80 | (Z,E)-α-Farnesene | 204 | 26560-14-5 | 1742 | 0.03 |
| | 2 | 25.03 | Calamenene | 202 | 483-77-2 | 1879 | 0.02 |
| | 3 | 16.98 | Alloocimene | 136 | 13877-91-3 | 1422 | 2.81 |
| | 4 | 16.59 | (Z)-3-Hexen-1-ol | 100 | 928-96-1 | 1402 | 4.83 |
| | 5 | 23.25 | (E)-Citral | 152 | 141-27-5 | 1768 | 0.19 |
| | 6 | 6.85 | Ethanol | 46 | 64-17-5 | 950 | 6.02 |
| | 7 | 16.49 | Neo alloocimene | 136 | 7216-56-0 | 1397 | 1.34 |
| | 8 | 10.18 | n-Hexanal | 100 | 66-25-1 | 1102 | 0.28 |
| | 9 | 15.87 | n-Hexanol | 102 | 111-27-3 | 1366 | 1.18 |
| | 10 | 21.09 | (E)-Caryophyllene | 204 | 87-44-5 | 1643 | 13.48 |
| | 11 | 19.02 | α-Copaene | 204 | 3856-25-5 | 1529 | 2.31 |
| | 12 | 22.41 | α-Humulene | 204 | 6753-98-6 | 1719 | 1.01 |
| | 13 | 13.44 | (Z)-β-Ocimene | 136 | 3338-55-4 | 1249 | 1.12 |
| | 14 | 11.94 | β-Myrcene | 136 | 123-35-3 | 1180 | 2.76 |
| | 15 | 23.70 | δ-Cardinene | 204 | 483-76-1 | 1796 | 0.14 |

"RT" indicates Retention Time;
"MW" indicates Molecular Weight;
"CAS #" indicates Chemical Abstract Number; and
"LRI" indicates Linear Retention Index.

simultaneously presented to the adult psyllids in the two extending olfactometer arms. The negative control for this experiment consisted of ~3.5 g of citrus flush alone (without DMDS) in each arm of the Y-tube olfactometer. In the second experiment, the test insects were presented with citrus or DMDS volatiles in one extending arm of the olfactometer and clean laboratory air in the other. In the first experiment, the number of $D.$ $citri$ that did not move from their point of release (defined as repelled) were quantified and compared with the number making upwind progress toward the source of volatiles (defined as attracted). In the second experiment, we compared the number of $D.$ $citri$ choosing arms containing a source of volatiles (defined as attracted) versus arms containing clean air (defined as repelled). The tested adult psyllids were individually released from the base of the olfactometer stem and given 300 seconds to exhibit a behavioral response. The arms of the olfactometer were rotated after three adult psyllids were tested and the entire system was cleaned after six psyllids had been tested. For each experiment, at least twenty adult psyllids were tested per treatment.

Figure 6:
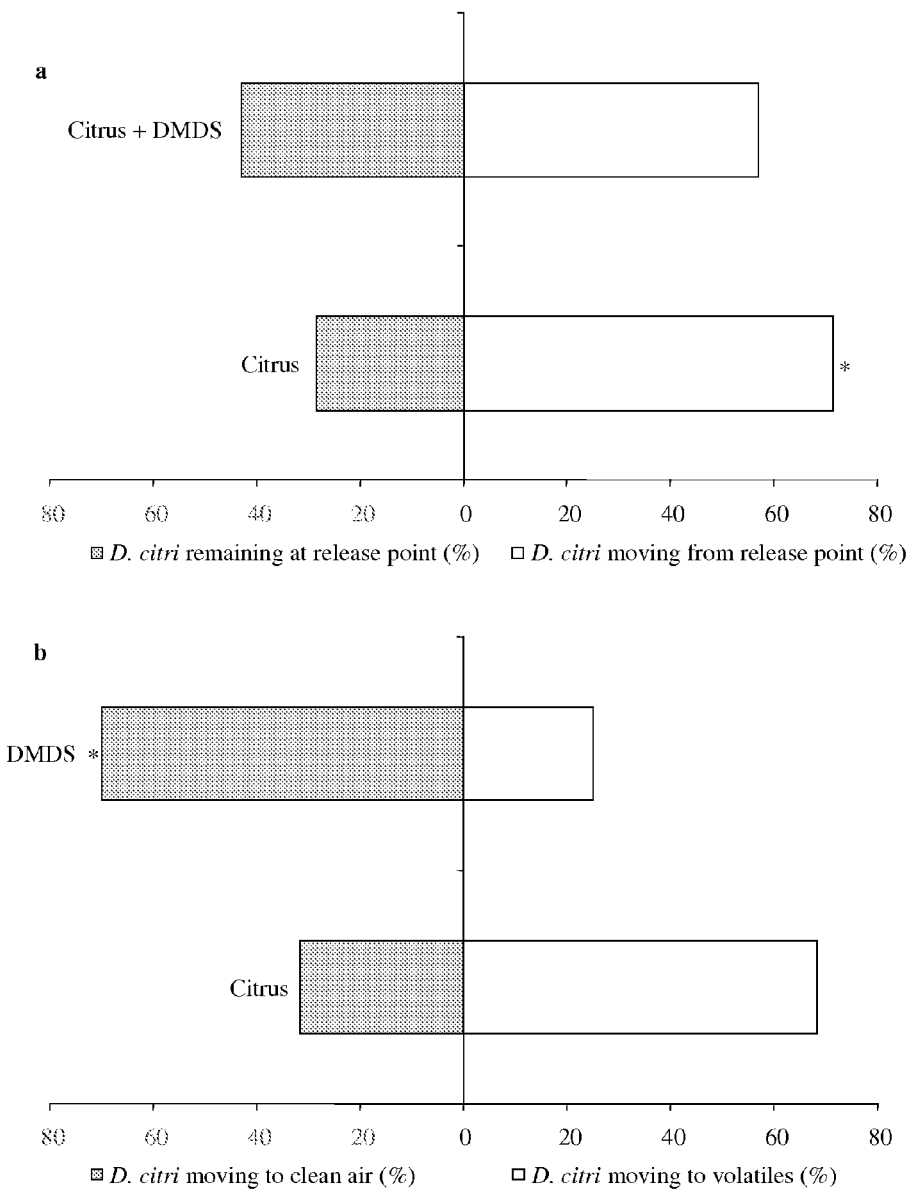

The proportion of $D.$ $citri$ responding to citrus volatiles co-released with DMDS was significantly ($\chi^2$=2.57, d.f.=1, P=0.109) lower than the proportion responding to citrus volatiles alone (FIG. 6$a$). Significantly ($\chi^2$=5.0, d.f.=1, P=0.025) more $D.$ $citri$ chose the arm of the Y-tube with throughput of clean air compared with the arm with DMDS (FIG. 3$b$). However, significantly ($\chi^2$=2.57, d.f.=1, P=0.108) more $D.$ $citri$ chose the arm with citrus volatiles compared with clean air (FIG. 6$b$). The above Y-tube olfactometer results support the contention that DMDS repels $D.$ $citri$ as DMDS significantly inhibited $D.$ $citri$'s response to citrus flush volatiles. Although, nearly 70% of $D.$ $citri$ were attracted to citrus compared with clean air, nearly 75% chose the arm releasing clean air versus DMDS. Also, addition of synthetic DMDS to citrus inhibited upward movement of psyllids to the normally attractive citrus host plant volatiles.

EXAMPLE 15

Data Analyses

Adult psyllids that oriented to any of the four arms of the olfactometer were categorized as attracted and those that remained in the olfactometer's central orifice (release point) until the 1.5 h experimental period elapsed as repelled. To compare the number of repelled psyllids between treatments, data were subjected to one-way analysis of variance (ANOVA) followed by Tukey's HSD test (P<0.05, SAS Institute Inc., 2003). Thereafter, the total number of attracted and repelled psyllids within each treatment was compared using Student's t-test analyses (P<0.05, SAS Institute Inc., 2003). Subsequently, data obtained for $D.$ $citri$ orientation to the four arms (two volatile sources and two laboratory air) was analyzed for each treatment using one-way step-wise ANOVA followed by Tukey's HSD test (P<0.05, SAS Institute Inc., 2003). The data obtained from the Y-tube olfactometer bioassays was analyzed using Chi-square ($\chi^2$) analyses (Parker, 1979) to compare between the numbers of attracted versus repelled $D.$ $citri$ (P<0.05).

The above-described embodiments and configurations are neither complete nor exhaustive. As will be appreciated, other embodiments of the invention are possible utilizing, alone or in combination, one or more of the features set forth above or described in detail below. In addition, the present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

LITERATURE CITED

1. Beattie, G. A. C.; Holford, P.; Mabberley, D. J.; Haigh, A. M.; Bayer, R.; Broadbent, P. In *Aspects and insights of Australia—Asia collaborative research on huanglongbing*, Proceedings of an International Workshop for Prevention of Citrus Greening Diseases in Severely Infested Areas, Ishigaki, Japan, 7-9 Dec. 2006, 2006; Multilateral Research Network for Food and Agricultural Safety: pp 47-64.
2. Reinking, O. A., Diseases of economic plants in southern China. *Philippine Agricultural* 1919, 8, 109-135.
3. Ewing, J.; Terry, R.; Curtis, W.; Erick, C.; Ganzenmuller, R., Citrus summary 2006-07 Florida Agricultural Statistics Service, USDA National Agricultural Statistics Service Florida Field Office, Orlando, Fla. p 55.
4. Stevens, K. L.; Brekke, J. E.; Stern, D. J., Volatile constituents in guava. *J. Agr. Food Chem.* 1970, 18, (4), 598-9.
5. MacLeod, A. J.; Gonzalez de Troconis, N., Volatile flavor components of guava. *Phytochemistry* 1982, 21, (6), 1339-42.
6. ldstein, H.; Schreier, P., Volatile constituents from guava (*Psidium guajava*, L.) fruit. *J. Agric. Food Chem.* 1985, 33, (1), 138-43.
7. Pino, J. A.; Ortega, A.; Rosado, A., Volatile constituents of guava (*Psidium guajava* L.) fruits from Cuba. *J. Essent. Oil Res.* 1999, 11, (5), 623-628.
8. Jordan, M. J.; Margaria, C. A.; Shaw, P. E.; Goodner, K. L., Volatile Components and Aroma Active Compounds in Aqueous Essence and Fresh Pink Guava Fruit Puree (*Psidium guajava* L.) by GC-MS and Multidimensional GC/GC-O. *J. Agric. Food Chem.* 2003, 51, (5), 1421-1426.
9. Soares, F. D.; Pereira, T.; Maio Marques, M. O.; Monteiro, A. R., Volatile and non-volatile chemical composition of the white guava fruit (*Psidium guajava*) at different stages of maturity. *Food Chem.* 2006, 100, (1), 15-21.
10. Smith, R. M.; Siwatibau, S., Sesquiterpene Hydrocarbons of Fijian Guavas. *Phytochemistry* 1975, 14, (9), 2013-2015.
11. Osman, A. M.; EI-Garby Younes, M.; Sheta, A. E., Chemical examination of local plants. Part VII. *Psidium guajava* L. leaf extracts. *Egyptian Journal of Chemistry* 1975, 18, (2), 347-52.
12. Pino, J. A.; Aguero, J.; Marbot, R.; Fuentes, V., Leaf oil of *Psidium guajava* L. from Cuba. *Journal of Essential Oil Research* 2001, 13, (1), 61-62.
13. Ogunwande, I. A.; Olawore, N. O.; Adeleke, K. A.; Ekundayo, O.; Koenig, W. A., Chemical composition of the leaf volatile oil of *Psidium guajava* L. growing in Nigeria. *Flavour and Fragrance Journal* 2003, 18, (2), 136-138.
14. Fluck, H., Intrinsic and extrinsic factors affecting the production of secondary plant products. In *Chemical plant taxonomy*, Swain, T., Ed. Academic Press: London, 1963; p 167186.
15. Ehrlich, P. R.; Raven, P. H., Butterflies and plants: a study in coevolution. *Evolution* 1964, 18, 586-608.
16. Rauscher, M. D., Natural selection and the evolution of plant-insect interactions. In *Insect Chemical Ecology*, MB, R. B. a. I., Ed. Chapman and Hall: New York, 1992; pp 20-88.
17. Dugravot, S.; Mondy, N.; Mandon, N.; Thibout, E., Increased sulfur precursors and volatiles production by the leek *Allium porrum* in response to specialist insect attack. *Journal of Chemical Ecology* 2005, 31, (6), 1299-1314.
18. Balandrin, M. F.; Lee, S. M.; Klocke, J. A., Biologically active volatile organosulfur compounds from seeds of the neem tree, Azadirachta indica (Meliaceae). *J. Agric. Food Chem.* 1988, 36, (5), 1048-54.
19. Huang, Y.; Chen, S. X.; Ho, S. H., Bioactivities of methyl allyl disulfide and diallyl trisulfide from essential oil of garlic to two species of stored-product pests, *Sitophilus zeamais* (Coleoptera: Curculionidae) and *Tribolium castaneum* (Coleoptera: Tenebrionidae). *Journal of economic entomology* 2000, 93, (2), 537-43.
20. Florida Department of Agriculture and Consumer Services, 2002-2003 Annual report Bureau of Citrus Budwood Registration 2003; p 109.
21. Dugravot, S.; Thibout, E.; Abo-Ghalia, A.; Huignard, J., How a specialist and a non-specialist insect cope with dimethyl disulfide produced by *Allium porrum*. *Entomologia Experimentalis Et Applicata* 2004, 113, (3), 173-179.
22. Pino, J. A.; Marbot, R.; Vazquez, C., Characterization of volatiles in Costa Rican guava [*Psidium friedrichsthalianum* (Berg) Niedenzu] fruit. *J Agric Food Chem* 2002, 50, (21), 6023-6.
23. Nishida, R.; Shelly, T. E.; Whittier, T. S.; Kaneshiro, K. Y., Alpha-copaene, a potential rendezvous cue for the mediterranean fruit fly, *Ceratitis capitata? Journal of Chemical Ecology* 2000, 26, (1), 87-100.
24. Vargas, R. I.; Harris, E. J.; Nishida, T., Distribution and seasonal occurrence of *Ceratitis capitata* (Wiedemann) (Diptera: Tephritidae) on the Island of Kauai in the Hawaiian Islands. *Environ. Entomol.* 1983, 12, 303-310.
25. Vargas, R. I.; Nishida, T.; Beardsley, J. W., Distribution and abundance of *Dacus dorsalis* (Diptera: Tephritidae) in native and exotic forest areas on Kauai. *Enuiron. Entomol.* 1983, 12, 1185-1189.
26. Baranowski, R.; Glenn, H.; Sivinski, J., Biological Control of the Caribbean Fruit Fly (Diptera: Tephritidae). *The Florida Entomologist* 1993, 76, (2), 245-251.
27. Binder, R. G.; Flath, R. A., Volatile components of pineapple guava. *J. Agric. Food Chem.* 1989, 37, (3), 734-6.
28. Hwang, J. S.; Yen, Y. P.; Chang, M. C.; Liu, C. Y., Extraction and identification of volatile components of guava fruits and their attractiveness to Oriental fruit fly, *Bactrocera dorsalis* (Hendel). *Zhiwu Baohu Xuehui Huikan* 2002, 44, (4), 279-302.
29. Manjunath, K. L; Halbert, S. E; Ramadugu, C.; Webb S.; and Lee R. F.; Detection of '*Candidatus Liberibacter asiaticus*' in *Diaphorina citri* and Its Importance in the Management of Citrus Huanglongbing in Florida, *Bactrocera dorsalis* (Hendel). *Zhiwu Baohu Xuehui Huikan* 2002, 44, (4), 279-302.
30. Agrawal A A & Karban R (1999) Why induced defenses may be favored over constitutive strategies in plants. The Ecology and Evolution of Inducible Defenses (ed. By R Tollrian & CD Harvell), pp. 45-61. Princeton University Press, Princeton. Arthur F H (1996) Grain protectants: current status and prospects for the future. Journal of Stored Products Research 32: 293-302.
31. Aubert B (1987) *Trioza erytreae* Del Guercio and *Diaphorina citri* Kuwayama (Homoptera: Psylloidea), the two vectors of citrus greening disease: biological aspects and possible control strategies. Fruits 42: 149-162.
32. Auger J, Cadoux F & Thibout E (1999) *Allium* spp. thiosulfinates as substitute fumigants for methylbromide. Pesticide Science 55: 200-202. Avé DA, Gergoy P & Tingey, WM (1987) Aphid repellent sesquiterpenes in glandular trichomes of *Solanum berthauffii* and *S. tuberosum*. Entomologia Experimentalis et Applicata 44: 131-138.
33. Bove J M (2006) Huanglongbing: a destructive, newly-emerging, century-old disease of citrus. Journal of Plant Pathology 88: 7-37.
34. Buitendag C H & von Broembsen La. (1993) Living with citrus greening in South Africa. Proceedings of the Twelfth Conference of the International Organization of Citrus Virologists, pp. 269-273. New Delhi, IOCV & University of California, Riverside.
35. Capoor S P (1963) Decline of citrus trees in India. Bulletin National Institute of Science India 24: 48-64.
36. Childers C C & Rogers M E (2005) Chemical control and management approaches of the Asian citrus psyllid, *Diaphorina citri* Kuwayama (Hemiptera: Psyllidae) in Florida citrus. Proceedings of the Florida State Horticulture Society 118: 49-53.
37. Clerici W J & Fechter L D (1991) Effects of chronic carbon disulfide inhalation on sensory and motor function in the rat. Neurotoxicology and Teratology 13: 249-255.
38. Dugravot S, Grolleau F, Macherel D, Rochetaing A, Hue B, Stankiewicz M, Huignard J & Lapied B (2003) Dimethyl disulfide exerts insecticidal neurotoxicity through mitochondrial dysfunction and activation of insect KATP channels. Journal of Neurophysiology 90: 259-270.
39. Dugravot S, Sanon A, Thibout E & Huignard J (2002) Susceptibility of *Callosobruchus maculatus* (Coleoptera: Bruchidae) and its parasitoid Dinarmus basalis (Hymenoptera: Pteromalidae) to sulphur-containing compounds: consequences on biological control. Environmental Entomology 31: 550-557.

41. Gouinguene S, Alborn H & Turlings T C J (2003) Induction of volatile emissions in maize by different larval instars of *spodoptera* littoralis. Journal of Chemical Ecology 29: 145-162.
42. Halbert S E (1998) Entomology Section Tri-ology (May-June 1998) 37: 6-7.
43. Halbert S E, Brown L & Dixon W (1998) Asian citrus psyllid update. Florida Department of Agriculture & Consumer Services Division of Plant Industry 18 Nov.
44. Halbert S E & Manjunath K L (2004) Asian citrus psyllids (Sternorrhyncha: Psyllidae) and greening disease of citrus: a literature review and assessment of risk in Florida. Florida Entomologist 87: 330-353.
45. Hall D G (2008) Biology, history and world status of *Diaphorina citri*. Taller Internacional Sobre Huanglongbing de los Citricos. Hermosillo, Sonora. Mexico I: 1-11.
46. Hall D G & Albrigo L G (2007) Estimating the relative abundance of flush shoots in citrus, with implications on monitoring insects associated with flush. Horticultural Science 42: 364-368.
47. Hall D G, Gottwald T R, Chau N M, Ichinose K, Dien L Q & Beattie G A C (2008) Greenhouse investigations on the effect of guava on infestations of Asian citrus psyllid in citrus. Proc. Florida State Horticulture Society (In Press).
48. Hall D G, Gottwald T R, Chau N M, Ichinose K, Dien L Q & Beattie G A C (2007) Intercropping of citrus and guava trees for management of huanglongbing. (Abstract) Florida Entomological Society Annual Meeting, July 15-18, Sarasota, Florida, # 72 http://www.ars.usda.goviresearch/publications/publications.htm?SEQ NO 115=212117
49. Hardie J J, Storer R, Nottingham S F, Peace L, Harrington R, Merritt L, Wadhams L J & Wood D K (1994) The interaction of sex pheromone and plant volatiles for field attraction of male bird-cherry aphid, *Rhopalosiphum padi*. Proceedings of the Brighton Crop Protection Conference: Pests and Diseases 3: 1223-1230.
50. Hrutfiord B F, Hopley S M & Gara R I (1974) Monoterpenes in sitka spruce: within tree and seasonal variation. Phytochemisty 13: 2167-2170.
51. Isaacs R, Hardie J, Hick A J, Pye B J, Smart L E, Wadhams L J & Woodcock C M (1993) Behavioral responses of *Aphis fabae* to isothiocyanates in the laboratory and field. Pesticide Science 39: 349-355.
52. Jackson D L & Dixon A F G (1996) Factors determining the distribution of the green spruce aphid, *Elatobium abietinum* on young and mature needles of spruce. Ecological Entomology 21: 358-364.
53. Jackson D L, Jarosik V & Dixon A F G (1996) Resource partitioning and tolerance of monoterpenes in four species of spruce aphid. Physiological Entomology 21: 242-246.
54. Kalule T & Wright D J (2004) The influence of cultivar and cultivar-aphid odours on the olfactory response of the parasitoid *Aphidius colemani*. Journal of Applied Entomology 128: 120-125.
55. Karban R & Baldwin I T (1997) Induced responses to herbivory. University of Chicago Press, Chicago, USA. 319 pp.
56. Kasperbauer M J & Loughrin J H (2004) Morphogenic light reflected to developing cotton leaves affects insect-attracting terpene concentrations. Crop Science. 44: 198-203.
57. Koizumi M, Prommintara M, Linwattana G & Kaisuwan T (1993) Field evaluation of citrus cultivars for greening resistance in Thailand. (ed. by P. Moreno, JV da Graga & LW Timmer), pp. 274-279. Proceedings of the $12^{th}$ Conference of the International Organization of Citrus Virologists. University of California, Riverside.
58. Loomis W D & Croteau R (1980) Biochemistry of terpenoids (ed. by PK Stumpf & EE Conn), pp. 363-418. The Biochemistry of Plants: A Comprehensive Treatise IV, Academic Press, New York.
59. McFarland C D & Hoy M A (2001) Survival of *Diaphorina citri* (Homoptera: Psyllidae), and its two parasitoids, *Tamarixia radiata* (Hymenoptera: Eulophidae) and *Diaphorencyrtus aligarensis* (Hymenoptera: Encyrtidae) under different relative humidities and temperature regimes. Florida Entomologist 84: 227-233.
60. Michaud J P (2002) Biological control of Asian citrus psyllid, *Diaphorina citri* (Homoptera: Psyllidae), in Florida: a preliminary report. Entomological News 113: 216-222.
61. Michaud J P (2004) Natural mortality of Asian citrus psyllid (Homoptera: Psyllidae) in central Florida. Biological Control 29: 260-269.
62. Michaud J P (2001) Numerical response of *Oila v-nigrum* (Coleoptera: Coccinellidae) to infestations of Asian citrus psyllid (Hemiptera: Psyllidae), in Florida. Florida Entomologist 84: 608-612.
63. Michaud J P & Olsen L E (2004) Suitability of Asian citrus psyllid, *Diaphorina citri*, as prey for ladybeetles (Coleoptera: Coccinellidae). BioControl 49: 417-431.
64. Onagbola E O (2008) Studies on the biology and host location behavior of *Pteromalus cerealellae* (Ashmead) (Hymenoptera: Pteromalidae), a parasitoid of *Callosobruchus maculatus* (F.) (Coleoptera: Chrysomelidae). Ph.D dissertation, Auburn University, Auburn, Ala., USA. 272 pp.
65. Parker R E (1979) Introductory statistics for biology. $2^{nd}$ ed. Cambridge University Press, Cambridge.
66. Pettersson J (1970) An aphid sex attractant. Entomologia Scandinavica 1: 63-73.
67. Pettersson J, Pickett J A, Pye B J, Quiroz A, Smart L E, Wadhams L J & Woodcock C M (1994) Winter host component reduces colonisation by bird-cherry-oat aphid, *Rhopalosiphum padi* (L.) (Homoptera, Aphididae), and other aphids in cereal fields. Journal of Chemical Ecology 20: 2565-2574.
68. Pickett J A, Wadhams L J, Woodcock C M & Hardie J (1992) The chemical ecology of aphids. Annual Review of Entomology 37: 67-90.
69. Powell C A, Burton M S, Pelpsi M A & Bullock R C (2007) Effects of insecticide on Asian citrus psyllid (Hemiptera: Psyllidae) populations in a Florida citrus grove. Plant Health Progress (Plant Management network), 4 pp.
70. Rogers M E & Timmer L W (2007) Florida pest management guide update. Citrus Industry 88: 11-12.
71. Roistacher C N (1996) The economics of living with citrus diseases: Huanglongbing (greening) in Thailand. (ed. by JV da Graça, P Moreno & R K Yokomi), pp. 279-285. Proceedings of the $13^{th}$ Conference of the International Organization of Citrus Virologists. University of California, Riverside.
72. Rouseff R L, Onagbola E O, Smoot J M & Stelinski L L (2008) Sulfur volatiles in guava (*Psidium guajava* L.) leaves: possible defense mechanism. Journal of Agricultural and Food Chemistry 56: 8905-8910.
73. SAS Institute Inc (2003) SAS user's guide: statistics. Release 9.10, Cary, N.C.
74. Srinivasan R, Hoy M A, Singh R & Rogers M E (2008) Laboratory and field evaluations of silwet L-77 and kinetic alone and in combination with imidacloprid and abamectin for the management of the Asian citrus psyllid, *Diaphorina citri* (Hemiptera: Psyllidae). Florida Entomologist 91: 87-100.
75. Stansly P A & Rogers M E (2006) Managing Asian citrus psyllid populations. Citrus Industry 87: 17-19.
76. Su H J & Huang A (1990) The nature of liikubin organism, life cycle morphology and possible strains. Proceedings of the 4$^{th}$ Asia-Pacific International conference on Citriculture, Texeira 16: 106-111.
77. Tabacova S & Balabaeva L (1980) Subtle consequences of prenatal exposure to low carbon disulphide levels. Archives of Toxicology Supplement 4: 252-254.
78. Tang Y Q (1989) A preliminary survey on the parasite complex of *Diaphorina citri* Kuwayama (Homoptera: Psyllidae) in Fujian. (ed. by B Aubert, K Chung & C Gonzales), pp. 10-16. Proceedings of the 2$^{nd}$ FAO-UNDP Regional Workshop on the Asian-Pacific Citrus Greening Disease.
79. Tsai J H, Chen Z Y, Shen C Y & Jin K X (1988) Mycoplasmas and fastidious vascular prokaryotes associated with tree diseases in China. (ed. by C Hiruki), pp. 69-240. Tree Mycoplasmas and *Mycoplasma* Disease. The University of Alberta Press, Edmonton, AB, Canada.
80. van Oosten A M, Gut J, Harrewijn P & Piron P G M (1990) Role of farnesene isomers and other terpenoids in the development of different morphs and forms of the aphids *Aphis fabae* and Myzuspersicae. Acta Phytopathologica et Entomologia Hungarica 25: 331-342.
81. Vet L E M, Van Lenteren J C, Heymans M & Meelis E (1983) An airflow olfactometer for measuring olfactory responses of hymenopterous parasitoids and other small insects. Physiological Entomology 8: 97-106.
82. Wallin K F & Raffa K F (2004) Feedback between individual host selection behavior and population dynamics in an eruptive herbivore. Ecological Monographs 74: 101-116.
83. Wenninger E J, Stelinski L L & Hall D G (2009) Roles of olfactory cues, visual cues, and mating status in orientation of *Diaphorina citri* Kuwayama (Hemiptera: Psyllidae) to four different host plants. Environmental Entomology 38: 225-234.

The invention claimed is:

1. A method for repelling or killing vectors of citrus greening disease comprising:
    exposing the vectors to an effective amount of at least one volatile compound to repel or kill at least one of the vectors of citrus greening disease wherein the at least one volatile compound comprises hydrogen sulfide, methanethiol, sulfur dioxide, dimethyl sulfide, dimethyl disulfide, methional, or dimethyl trisulfide, or combinations thereof.

2. The method of claim 1, wherein the at least one volatile compound comprises dimethyl disulfide.

3. The method of claim 1, wherein the at least one volatile compound is obtained from crushed leaves of *Psidium guajava* L.

4. A method of imparting, augmenting or enhancing the repellent effect of a composition for repelling vectors carrying citrus greening disease comprising:
    incorporating into the composition at least one volatile compound in an amount effective to repel or kill at least one of the vectors carrying citrus greening disease; wherein the at least one volatile compound comprises hydrogen sulfide, methanethiol, sulfur dioxide, dimethyl sulfide, dimethyl disulfide, methional, or dimethyl trisulfide, or combinations thereof.

5. The method of claim 4, wherein the at least one volatile compound is dimethyl disulfide.

6. The method of claim 4, wherein the the at least one volatile compound is obtained from crushed leaves of *Psidium guajava* L.

7. A method for repelling or killing vectors of citrus greening disease comprising:
    exposing the vectors to an effective amount of a dimethyl disulfide composition to repel or kill at least one of the vectors of citrus greening disease.

8. The method of claim 7, wherein the dimethyl disulfide composition further comprises an agriculturally acceptable carrier oil, and wherein the concentration of dimethyl disulfide in the agriculturally acceptable carrier oil is from 2 to 8 µg/ml.

* * * * *